(12) United States Patent
Levy et al.

(10) Patent No.: US 6,207,859 B1
(45) Date of Patent: Mar. 27, 2001

(54) STABILIZATION AND TRANSPORT OF α, β-UNSATURATED CARBOXYLIC ACID AND REMOVAL OF STABILIZER

(75) Inventors: Leon B. Levy, Corpus Christi; Edward F. Dougherty, League City; Charles C. Hobbs, Jr., Corpus Christi; Jerome F. Perez, Houston; Mark O. Scates, Friendswood; Madan Singh, Corpus Christi, all of TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/404,415

(22) Filed: Sep. 23, 1999

Related U.S. Application Data

(62) Division of application No. 09/165,674, filed on Oct. 2, 1998, now Pat. No. 6,046,357.

(51) Int. Cl.$^7$ .................................................. C07C 57/02
(52) U.S. Cl. ........................... 562/598; 562/600; 562/510
(58) Field of Search .................................. 562/510, 398, 562/600

(56) References Cited

U.S. PATENT DOCUMENTS

| | | | |
|---|---|---|---|
| 4,507,495 | 3/1985 | Dougherty et al. | 560/205 |
| 4,542,231 | 9/1985 | Dougherty et al. | 560/4 |
| 4,814,493 | 3/1989 | Dougherty et al. | 560/205 |

FOREIGN PATENT DOCUMENTS

| | | |
|---|---|---|
| 0 371 748 | 11/1989 | (EP) . |
| 51-098211 | 8/1976 | (JP) . |
| 5-017512 | 1/1993 | (JP) . |
| 5-140027 | 6/1993 | (JP) . |
| 6-211735 | 8/1994 | (JP) . |
| 8310979 | 11/1996 | (JP) . |

OTHER PUBLICATIONS

Kurland, J.J., Bryant D.R., Plant/Operations Progress, 6(4), 203–207, Oct. 1987.

*Primary Examiner*—Samuel Barts
(74) *Attorney, Agent, or Firm*—M. Susan Spiering

(57) ABSTRACT

A process for inhibiting free-radical polymerization of an alpha,beta-unsaturated (α,β-unsaturated) carboxylic acid, and for providing desired grade α,β-unsaturated carboxylic acid for use following storage and transport is described herein. In particular, bulk storage and shipment such as with overseas transport is described. The process comprises combining the α,β-unsaturated carboxylic acid with a phenolic inhibitor and a coinhibitor to form an inhibited mixture, storing the inhibited mixture, transporting the inhibited mixture, and removing the coinhibitor to provide the desired grade α,β-unsaturated carboxylic acid for use. In preferred embodiments, the α,β-unsaturated carboxylic acid is acrylic acid, the phenolic inhibitor is p-methoxyphenol, the coinhibitor is manganese cation, and removal of the coinhibitor is carried out using an ion exchange resin.

27 Claims, No Drawings

STABILIZATION AND TRANSPORT OF α, β-UNSATURATED CARBOXYLIC ACID AND REMOVAL OF STABILIZER

This is a divisional application of prior U.S. Ser. No. 09/165,674, filed Oct. 2, 1998, now U.S. Pat. No. 6,046,357.

FIELD OF THE INVENTION

The present invention relates to stabilization of alpha, beta-unsaturated (α,β-unsaturated) carboxylic acids in general, and acrylic acid in particular, to avoid free-radical polymerization. More particularly, it concerns such stabilization during storage and transport using a phenolic inhibitor and a cationic coinhibitor followed by removal of the coinhibitor after storage and transport to provide a desired grade of α,β-unsaturated carboxylic acid to a recipient. Stabilization of an α,β-unsaturated carboxylic acid in the presence of a polymerization initiator is also provided.

BACKGROUND OF THE INVENTION

In recent years there has been an increasing interest in the development of the world market for monomers of α,β-unsaturated carboxylic acids in general, and acrylic acid in particular. Much of this interest reflects the importance of useful polymers which can be produced from these α,β-unsaturated carboxylic acids for products such as paints, coatings, lacquers, water treatment, secondary oil recovery, and superabsorbent polymers.

Although acrylate esters are currently stored and transported on a routine basis, it is well recognized that acrylic acid is significantly more reactive than acrylic esters and the same methods employed for the storage and transport of the esters are not applicable to the acid. Acrylic acid is one of the most reactive of the common vinyl monomers. Due to his reactivity, glacial acrylic acid in particular has only been marine shipped in bulk (i.e., in a ship's hold tank) once. In the 1970's, Union Carbide attempted to ship a cargo of glacial acrylic acid across the Atlantic in the ship Alchemist. There was a runaway polymerization at sea and the ship was seriously damaged (Kurland, J. J., and Bryant, E. R. *Plant/Operations Progress* 6(4), 203–207 (October, 1987)). Since then, to the present inventor's knowledge, no one has attempted a bulk marine shipment of glacial acrylic acid. Acrylic acid, however, inhibited with ≧100 ppm phenothiazine (PTZ) is currently shipped over land and by marine shipment.

The risk of bulk marine shipments of glacial acrylic acid has been found to be unacceptably high. This is due, in part, to the limitations on safety procedures which can be implemented should a runaway polymerization occur at sea. On land, emergency personnel can respond to such an incident and evacuations may be conducted if necessary. At sea, these procedures are much more difficult, if not impossible, placing the crew at increased risk should a runaway polymerization occur. Another risk factor for marine shipment is that, in general, longer time periods are required for the transport than for land shipment. This further increases the risk of a runaway polymerization.

Inhibitors of polymerization include PTZ and phenolic inhibitors such as hydroquinone (HQ) and p-methoxyphenol, which is the monomethyl ether of hydroquinone (MEHQ). While these phenolic inhibitors are effective for acrylic acid significantly more of the phenolic inhibitor is required to achieve the same level of inhibition as PTZ. The phenolic inhibitors also require dissolved oxygen in order to be effective. This requirement could limit their use for storage and transport due to the possibility of inadvertent heating or the presence of unexpected polymerization inducers which could exhaust the available oxygen and consequently lead to runaway polymerization.

Published JP patent application No. 51-98211/1976 (21117/1975) relates to a method of preventing polymerization of an α,β-unsaturated carboxylic acid by addition of certain manganese salts. Generally, however, such materials are not useable because they are too unreactive. JP 51-98211 does not teach removal of the Mn to allow usage of the acid.

Japanese published application 5-140027, (application no. 4-133351) relates to a method of inhibiting polymerization of an α,β-unsaturated carboxylic acid by addition of a threefold system including phenol, hindered phenol, and Mn salt.

Published JP application no. 08-310979 (JP 8310979) relates to purification of a vinyl monomer by removing polymerization inhibitors with a certain adsorbent such as alumina, silica gel, molecular sieve, activated carbon, ion exchange resin, chelate resin, zeolite, and acid clay.

JP publication 06-211735 (JP 6211735A) relates to producing methacrylic acid and prevention of polymerization of methacrylic acid during transportation and storage.

JP publication 05-017512 (JP 5017512A) relates to prevention of polymerization of an α,β-unsaturated carboxylic acid by addition of p-phenylenediamine derivative and a manganese compound.

EP 371748 relates to inhibition of polymerization during distillation of monomers by means of a phenolic inhibitor and a manganese or cerium alkanoate of certain monocarboxylic acid.

US patents describing Mn and/or Ce as inhibitors for ester production wherein acrylic acid is employed as starting material are U.S. Pat. No. 4,814,493, 4,507,495, and 4,542,231. These patents do not address storage and transport of or removal of metals in acrylic acid.

Because of the risk factors regarding polymerization of α,β-unsaturated carboxylic acid particularly for storage and shipping in bulk, and the need for desired grade product after storage and shipment, known procedures are not completely satisfactory.

SUMMARY OF THE INVENTION

The present invention provides a process for inhibiting free-radical polymerization of an α,β-unsaturated carboxylic acid, and for providing desired grade α,β-unsaturated carboxylic acid for use following storage and transport. The method comprises combining the α,β-unsaturated carboxylic acid with a phenolic inhibitor and a coinhibitor to form an inhibited mixture, storing the inhibited mixture, transporting the inhibited mixture, and removing the coinhibitor to provide the desired grade α,β-unsaturated carboxylic acid for use. The coinhibitor is a metal cation having at least two valence states which are interconvertible via electron transfer reactions with other species (e.g., radicals) in the mixture. The α,β-unsaturated carboxylic acid has structure I:

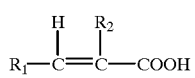

wherein $R_1$ is H, or lower alkyl; and $R_2$ is H, or methyl. The process can be carried out in the presence or absence of air.

A further embodiment of the present invention is a process for inhibiting free-radical polymerization of an α,β-unsaturated carboxylic acid for storage and transport, the acid inadvertently contaminated with a polymerization initiator. The method comprises combining the α,β-unsaturated carboxylic acid with a phenolic inhibitor and a coinhibitor in the presence of air to form an inhibited mixture, storing the inhibited mixture, and transporting the inhibited mixture. The coinhibitor is a metal cation having at least two valence states which are interconvertible via electron transfer reactions with other species (e.g., radicals) in the mixture, and the α,β-unsaturated carboxylic acid has structure I:

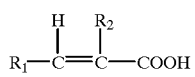

wherein $R_1$ is H, or lower alkyl; and $R_2$ is H, or methyl. Air, in particular dissolved oxygen, is present in the process if inadvertent presence of a polymerization initiator is possible.

As used herein, "inadvertently contaminated with a polymerization initiator" means that the α,β-unsaturated carboxylic acid is unintentionally exposed to an agent that promotes the polymerization of the acid. This unintentional exposure may occur due to presence of residual cleaning agents in a tanker, or may occur due to improper labeling of a tanker regarding its previous cargo, for example.

A process for inhibiting free-radical polymerization of acrylic acid for storage and transport, and providing desired grade acrylic acid for use following storage and transport is a preferred embodiment of the present invention. The process comprises combining the acrylic acid with p-methoxyphenol and a manganese (Mn) cation (in the form of a Mn salt) to form an inhibited mixture, storing the inhibited mixture, transporting the inhibited mixture, and removing the manganese cation using conventional methods known in the art to provide the desired grade acrylic acid for use.

A particularly preferred embodiment of the present invention is a process for inhibiting free-radical polymerization of glacial acrylic acid for storage and transport, and providing glacial acrylic acid for use following storage and transport. The method comprises combining the glacial acrylic acid with p-methoxyphenol and a manganese cation to form an inhibited mixture, storing the inhibited mixture, transporting the inhibited mixture (e.g., as a rail or marine shipment), and removing the manganese cation by techniques known in the art, such as by using a sulfonic acid based ion exchange resin, to provide glacial acrylic acid for use.

The terms "a" and "an" as used herein mean "one or more" when used in this application, including the claims.

DETAILED DESCRIPTION OF THE PREFERRED EMBODIMENTS

The present invention provides a process that lowers risk for personnel and equipment in the bulk storage and/or transport of an α,β-unsaturated carboxylic acid and provides for a desired grade α,β-unsaturated carboxylic acid following storage and/or transport. The invention also provides a process that lowers risk in the bulk storage and/or transport of an α,β-unsaturated carboxylic acid in the inadvertent presence of a polymerization initiator. As shown herein, certain metal cations are powerful inhibitor synergists with phenolic inhibitors to essentially prevent polymerization of acrylic acid, an exemplary α,β-unsaturated carboxylic acid.

As used herein, "free-radical polymerization" means polymerization of an α,β-unsaturated carboxylic acid as initiated by free-radicals as opposed to dimerization or short-chain oligomerization as a result of an ionic reaction.

As used herein, "desired grade α,β-unsaturated carboxylic acid" means a grade of acid requested by a recipient for use. For example, the desired grade end-product acid may need to meet the standards of glacial acrylic acid.

As used herein, "storage and transport" means any length of time of holding the inhibited mixture in any volume and moving the inhibited mixture from one location to another over land or sea. Particularly envisioned for the present invention is the shipment by tankers of bulk inhibited mixtures of α,β-unsaturated carboxylic acid in overseas shipments.

As used herein, "removing the coinhibitor" means separating the metal cation from the inhibited mixture using any of a number of separation methods described herein, preferably, by ion exchange.

As used herein, "transport" means shipment over land, for example, by rail or truck, or shipment by sea in a ship's deck or hold tank.

α,β-unsaturated carboxylic acids: α,β-unsaturated carboxylic acids contemplated for inhibition in the present invention are acids subject to free-radical polymerization and have the formula:

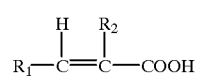

wherein $R_1$ is H, $C_{1-9}$ alkyl or cycloalkyl; and $R_2$ is H, or methyl. In a preferred embodiment, $R_1$ and $R_2$ are H (acrylic acid). In another preferred embodiment, $R_1$ is H, and $R_2$ is methyl (methacrylic acid). Per industry standard, glacial acrylic acid is considered to contain less than 0.05% $H_2O$ and have an assay of at least 99.8%.

Alkyl or cycloalkyl refers to a $C_{1-9}$ alkyl group such as methyl, ethyl, and straight-chain, branched or cyclic isomers of propyl or butyl.

Representative examples of α,β-unsaturated carboxylic acid contemplated for use with the present invention include acrylic acid, or methacrylic acid.

Phenolic Inhibitors: Phenolic inhibitors contemplated for use in the present invention are characterized by the presence of at least one other substituent on the benzene ring. Such other substituent serves to activate the phenolic inhibitor. Representative substituents include $C_{1-4}$ alkoxy such as methoxy and ethoxy. Other substituents include hydroxyl, sulfhydryl, amino, $C_{1-9}$ alkyl, phenyl, nitro, or N-linked amide, for example. Exemplary phenolic inhibitors include, but are not limited to, p-methoxyphenol (MEHQ), hydroquinone, or catechol such as tertiary butyl catechol or di-tertiary catechol. Preferably, the phenolic inhibitor is p-methoxyphenol.

Concentrations of inhibitors are given herein in parts per million (ppm) by weight. Phenolic inhibitors are typically added to result in concentrations ranging from about 10 ppm to about 1500 ppm, preferably about 20 ppm to about 1000 ppm, more preferably about 50 ppm to about 600 ppm, and most preferably, to result in a concentration of about 150 to about 250 ppm in the inhibited mixture.

Coinhibitor: The coinhibitor is a metal cation having at least two valence states which are interconvertible via electron transfer reactions with other species (e.g., radicals) in the mixture. That is, the two valence states have similar enough thermodynamic stabilities to allow a cyclic, or reversible, electron transfer to occur. Representative examples of such metal cations include, but are not limited to, manganese, copper, chromium, cerium, iron, or combinations thereof. Preferably, the metal cation is a cation of manganese (Mn), and the present invention will be described relative to Mn metal cation.

The coinhibitor is added such that the concentration present in the inhibited mixture is about 0.1 ppm to about 100 ppm, preferably about 1 ppm to about 50 ppm, more preferably about 1 ppm to about 20 ppm, or, most preferably about 2 ppm to about 10 ppm.

The metal cation is added in the combining step of the present invention in the form of a salt. Alternatively, although not preferred, the metal cation may be provided by adding the metal itself to the acid mixture. Anions contemplated for use in accordance with the present invention form salts with the metal cation that are soluble in the α,β-unsaturated carboxylic acid to be inhibited. Exemplary anions include, but are not limited to, carbonate, hydroxide, nitrate, acetate, propionate, butanoate, pentanoate, hexanoate, heptanoate, octanoate, nonanoate, acrylate, and methacrylate. Concentrations of metal cation are given herein in ppm by weight. In determining concentration of the desired salt, adjust the amount of salt based on the ratio of the molecular weight of the salt to the atomic weight of the metal. For example, 5 ppm Mn requires the addition of 22 ppm of manganous acetate tetrahydrate (5×245/55). The term manganese (Mn), as used herein, refers to the active species of metal cation.

Polymerization Initiator: As used herein, "polymerization initiator" means an agent that promotes the polymerization of an α,β-unsaturated carboxylic acid. Unintentional exposure to a polymerization initiator may occur due to presence of residual cleaning agents in a storage or transport tank due to incomplete cleaning, or may occur due to improper labeling of a tanker regarding its previous cargo, for example. Inadvertent contact of an α,β-unsaturated carboxylic acid cargo with a polymerization initiator due to incomplete hold tank cleaning is the risk that most distinguishes bulk marine shipment from other modes of shipment due to the difficulty of thoroughly cleaning marine tanks.

An initiator is characterized by the ability to initiate free-radical polymerization as a primary or secondary effect. An example of an initiator having a primary effect is a free-radical initiator that induces polymerization by direct introduction of free radicals into the monomers. Representative examples of such free-radical initiators include hydrogen peroxide, persulfate salts or benzoyl peroxide, for example. An example of an initiator having a secondary effect is a reagent or compound that reacts with the α,β-unsaturated carboxylic acid in such a way as to effect conditions that induce polymerization. An example is the induction of a local rise in temperature or exotherm upon reaction with the α,β-unsaturated carboxylic acid composition. A local exotherm can then induce polymerization of the mixture. Representative examples of secondary inducers include amines, or caustic agents such as sodium hydroxide, for example.

Although the processes for inhibiting polymerization of an inadvertently contaminated mixture require air in order to be effective (See Example 3), achieving presence of air is not a problem in most situations. The acrylic acid contemplated in the present invention will generally be equilibrated with air and, therefore, will have a concentration of about 55 ppm by weight of dissolved oxygen. This value will differ for other α,β-unsaturated carboxylic acids. Additionally, during storage and transport of these acids, a certain level of empty space (ullage) is required to allow for the expansion of the cargo due to heating or other unexpected conditions. This empty space together with the natural movement of transport further ensures presence of air.

Procedures: The inhibitor and coinhibitor may be added during process production of the acid, before storage, or before transport. They may be added in the form of a solid or powder, or although not preferred, in the form of a solution in water, or in a suitable organic solvent. They may be added together or successively; the order of addition has not been found to be relevant. Most commonly, the inhibitor and coinhibitor are added to the α,β-unsaturated carboxylic acid just prior to storage or transport. However, the phenolic inhibitor and/or the coinhibitor may also be added during the production process.

The process of the present invention is directed to the safe storage and transport of freshly manufactured acid. Typically, small amounts of peroxides build up in the stored acrylic acid. Addition of metal ions to peroxide-containing acrylic acid may induce polymerization. Hence, the present invention is not recommended for acids which have been stored for prolonged periods of time. These prolonged period of times vary per individual situation.

Temperature: Processes of the present invention are effective at ambient temperatures for land and/or marine shipment. Cargo temperatures of liquids in deck or hold tanks were monitored during trans-equatorial voyages and the highest temperature recorded was about 31° C. Long term thermal stability studies were carried out in air at about 39° C. (Example 2) and, after almost ten months of heating, none of the 26 samples had polymerized. In the absence of oxygen, no polymerization occurred for about 6 months.

Super-stabilization: Super-stabilization relative to acrylic acid and it is postulated relative to other α,β-unsaturated acids, is defined herein as an inhibitor or coinhibitor imparting a long enough induction period to polymerization (i.e., the time before onset of polymerization), such that most of the acid is converted to its dimer before any free radical (vinyl) polymerization has a chance to occur.

Thermal stability was tested at a range of about 60 C to about 100° C. At about 100° C. glacial acrylic acid continuously sparged with air was found to polymerize after about 6 hours with a very rapid, sharp exotherm. Regarding the dimers above, acrylic acid dimerizes via an ionic reaction (Michael addition) which is not impeded by the presence of free-radical inhibitors. The acrylic acid dimer is beta-acryloxypropionic acid. Higher molecular weight oligomeric Michael adducts are also formed depending on the time, temperature and conditions present. At about 100° C., it was found that about 50% of the acrylic acid is converted to dimer in about 2 days and about 70% in about 4 days.

Due to the fact that dimer formation is temperature and time dependent, and there are no known inhibitors for retarding or preventing this ionic reaction, different amounts of the dimer are present depending on the storage and/or transport conditions. Although dimer formation is not hazardous, it may affect the performance of the α,β-unsaturated carboxylic acid in some applications.

Induction periods: An induction period is defined herein as the period of time an α,β-unsaturated carboxylic acid must be held at experimental conditions in order for the onset of polymerization to occur.

Free-radical polymerization is recognized by an exotherm when the reaction occurs and by the white and opaque appearance of the polymer. The time and magnitude of the exotherm may be electronically measured. These methods are known to those of skill in the art.

Removal of the Coinhibitor: The coinhibitor is removed from the stored, shipped, and inhibited mixture to a level acceptable to the recipient of the cargo. As used herein, a level acceptable to the recipient of the cargo is defined as the "desired level". A desired level may range from removing very little of the metal cation to removing the metal cation such that the remaining concentration is less than or equal to about 100 ppb.

Methods for the removal of metal cations from an inhibited, stored, and shipped mixture include, for example, ion exchange, distillation, crystallization, extraction, reverse osmosis, or use of membrane systems. Ion exchange is a preferred method for coinhibitor removal as provided herein. Ion exchange resins contemplated for use in accordance with the present invention are cation exchange resins that lack activity for formation of Michael addition dimer or oligomers, lack affinity for the phenolic inhibitor so that the phenolic inhibitor is not removed from the mixture, and lack activity for induction of free-radical polymerization of the acid. Sulfonic acid-based resins from Rohm & Haas (Philadelphia, Pa.) such as Amberlyst-15 and IRC 50 were effective in the present studies with the Amberlyst-15 being most effective. It was found that a gem-diphosphonate-based resin, Diphonix (Eichrom Co. Darien, Ill.) was ineffective for removal of coinhibitor.

The processes provided herein find particular use in the transport of bulk shipments of acrylic acid by land or oceanic transport in the hold of a ship. Inhibited mixtures including acrylic acid are transported to a desired location and the coinhibitor removed after the shipment, either before delivery to a recipient or at a recipient's site.

While not wanting to be bound by theory, the present inventor believes the mechanism of action of the coinhibitor is catalytic in nature and unclear from the current art. It was not obvious to this artisan that the inventive process would lead to super-stabilization during transport of acids. Experimental evidence supporting the proposed mechanism follows. Phenolic inhibitors are relatively inefficient as free-radical traps at about 100° C. even in the presence of oxygen. The free-radicals which do escape initiate the co-oligomerization of the α,β-unsaturated carboxylic acid with oxygen. Subsequently, some of the peroxide bonds formed in this process decompose homolytically to produce more radicals. When a metal cation coinhibitor is added to the system, even in very small amounts, it has been demonstrated that no peroxide is formed and no oxygen or MEHQ is consumed. It has also been demonstrated that this coinhibition does not occur with PTZ and cationic metals. Additionally, the metal cations alone, in the absence of a phenolic inhibitor, do not inhibit acrylic acid.

These results indicate that the mechanism must be cyclic in nature, with the key species being regenerated, for the coinhibitor to be effective in such low concentrations. The proposed mechanism involves a very rapid reaction between the metal in a higher valence state and a carbon radical. The metal cation removes an electron from the radical, which then becomes a carbonium ion and the metal is reduced to its lower valence state. The carbonium ion reacts with an acrylate anion (from ionization of acrylic acid) to form a stable compound. There also exists a steady state concentration of substituted phenoxy radicals resulting from radicals abstracting hydrogen from the phenolic inhibitor. These phenoxy radicals are very electronegative and can quite readily become phenoxy anions in the presence of a reducing agent. Such a reducing agent is the lower valence metal ion which supplies an electron to the phenoxy radical. The phenoxy radical thereby becomes the phenoxy anion, which combines with a proton (from the acrylic acid ionization) to regenerate the phenolic inhibitor. Concurrently the metal is transformed to its higher valence state.

Mechanism 1: Metal/Phenolic Inhibitor Catalytic Cycles.

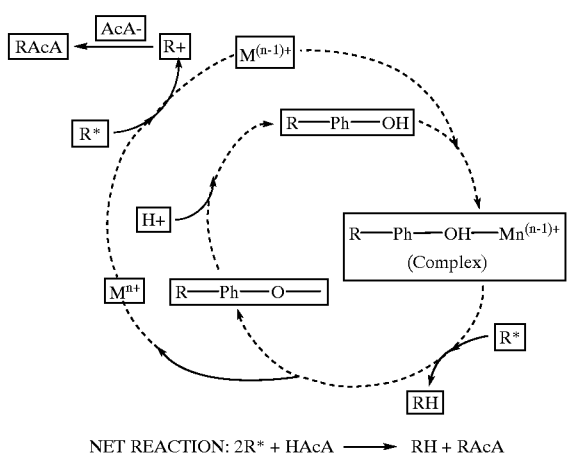

NET REACTION: 2R* + HAcA ⟶ RH + RAcA

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

One method involves simple visual inspection of a sample. The sample mixture, under a controlled atmosphere, is placed in a relatively small clear tube, typically about 3 inches long and the tube placed in a constant temperature bath. The sample is checked at regular time intervals depending on the estimated induction time. Free-radical polymerization of a small sample will occur essentially instantaneously and the induction time recorded accordingly.

Glacial acrylic acid employed in the present examples was obtained from Celanese Ltd., Clear Lake, Tex., and contained about 200 ppm MEHQ inhibitor.

The manganous acetate tetrahydrate was obtained from Hall Chemical Company, Cleveland, Ohio.

General Procedure

Stability tests in the presence of oxygen: (Test 1) A 28-cm-long×20-mm-diameter test tube fitted with a 19/38 female Standard Taper joint was charged with about 20 g of the acrylic acid sample to be tested. An Allihn condenser with a 19/38 male joint was connected to the top of the test tube. A 5-mm-diameter glass tube long enough to reach the bottom of the test tube was inserted down through the condenser, and the sample sparged with about 30 cc/minute of the desired gas (usually air) through this tube. A thermowell containing a thermocouple was also inserted through the condenser into the liquid. The test equipment was immersed in an oil bath set at the desired temperature. The onset of polymerization was marked by a rise in temperature, as indicated by the thermocouple in the liquid.

(Test 2) The acrylic acid sample to be tested is placed in a 51-mm-long×20-mm-outer diameter Pyrex test tube which tapered down to 15 cm of 0.25-inch-outer-diameter tubing. The tubing mouth was sealed with a Swagelock fitting, and the tube then immersed in an oil bath thermostated at the desired temperature. Agitation of the sample was achieved by means of an eccentrically rotating sample holder on a start/stop cycle. The onset of polymerization was signaled by the first appearance of turbidity in the sample.

Stability tests in the absence of oxygen: (Test 3) The acrylic acid stock sample was sparged with nitrogen for 1 hour in a 50 cc graduated cylinder. The sample test tube described in Test 2 above was purged with nitrogen for 30 minutes. A measured charge (1 to 10 cc) of the pre-sparged acrylic acid sample was introduced into the tube using a polyethylene/polypropylene syringe with a 14 gauge Teflon needle. The tube was sealed using a Swagelock fitting containing a rubber septum. A length of 2-mm glass tubing was inserted through the septum so that its end was below the level of the liquid. A 5-mm needle was also inserted through the septum to act as a vent. Nitrogen was bubbled through the 2 mm tubing into the liquid for about 30 minutes, after which both the tubing and the needle were simultaneously withdrawn. The test tube was then immersed in an oil bath thermostated at the desired temperature. The onset of polymerization was signaled by the first appearance of turbidity in the sample.

Except in cases were the number of samples is 1, results reported in Tables 1 and 2 are based on an average of as noted number of replicate sample runs.

EXAMPLE 1

Stabilizing Effect of Manganese to Free-Radical Polymerization

The present example demonstrates the effectiveness of manganese (Mn) as a coinhibitor with the phenolic inhibitor, p-methoxyphenol (MEHQ), at manganese concentrations as low as 5 ppm. The manganese was added as the manganous acetate tetrahydrate (about 22 ppm manganous acetate tetrahydrate=5 ppm manganese cation,) to glacial acrylic acid inhibited with about 200 ppm MEHQ. The data of Table 1 show that higher concentrations of manganese do not measurably improve the stability of the glacial acrylic acid.

TABLE 1

| CASE (# of sample runs) | TEMP., °C. (Atmosphere) | CO-INHIBITOR | AVER. INDUCTION PERIOD (hour) |
| --- | --- | --- | --- |
| A (5) | 100 (air) | Mn, 5 ppm | >38 ss |
| B (5) | 100 (air) | Mn, 10 ppm | >38 ss |
| C (4) | 100 (air) | none | 9 |

TABLE 1-continued

| CASE (# of sample runs) | TEMP., °C. (Atmosphere) | CO-INHIBITOR | AVER. INDUCTION PERIOD (hour) |
|---|---|---|---|
| D (5) | 100 (nitrogen) | Mn, 5 ppm | >37 ss |
| E (5) | 100 (nitrogen) | Mn, 10 ppm | >37 ss |
| F (2) | 100 (nitrogen) | none | 0.2 |
| Reference PTZ run | 100 (air or $N_2$) | PTZ, 100 ppm | ss | ss = super-stabilization; TEMP. = temperature; AVER. = average
The symbol ">" indicates that the experiment was terminated without any polymerization having taken place.

In cases A–C, samples of glacial acrylic acid containing about 5 and 10 ppm manganese were heated at about 100° C. under air for 38 hours with agitation. In cases A–B free-radical polymer did not form; the samples simply became slightly thick at about 36 hours due to the formation of Michael oligomers (dimer, trimer, etc.). Case C, illustrates controls without any manganese which polymerized after an average of 9 hours.

Cases D–F were repeats of cases A–C except that oxygen was scrupulously removed from the liquid and vapor space and the heating was carried out under a nitrogen blanket atmosphere. The 5 and 10 ppm manganese-containing samples (i.e. cases D & E) did not polymerize during 37 hours of heating. The manganese-free controls (i.e. case F) polymerized after an average of 11 minutes (MEHQ alone is known to need oxygen in order to function as an inhibitor)

These results confirm the super-stabilizing effect of manganese on the thermal stability of MEHQ-inhibited acrylic acid. Hence, under these conditions, 5 ppm manganese is at least as good an inhibitor as 100 ppm PTZ, as seen in the reference PTZ comparative run in Table 1. 100 ppm PTZ is an inhibitor and concentration commonly used for bulk transoceanic shipments of acrylic acid.

EXAMPLE 2

Stabilizing Effect at Shipping Temperatures

Cargo temperatures of liquids in hold tanks were monitored during trans-equatorial voyages and the highest temperature recorded was about 31° C. (88° F.). In order to confirm that manganese has a stabilizing effect on glacial acrylic acid in this temperature regime, long term thermal stability studies at about 39° C. (102° F.) under air were carried out on acrylic acid containing about 200 ppm MEHQ and 2.5, 5 and 10 ppm manganese. After 308 days (about 10 months) of heating, none of the total of 26 samples had polymerized. A similar test is presently being carried out in the absence of oxygen. 185 days (about 6 months) of heating have passed without any of these samples having polymerized.

The studies in this example are pertinent to both marine and land shipment.

EXAMPLE 3

Stabilization in the Presence of Polymerization Initiators

In this example, the stabilization of glacial acrylic acid containing about 200 ppm MEHQ and manganese was examined. Data are provided in Table 2.

TABLE 2

| CASE (# samples run/ sample size, cc) | TEMP., °C. (Atmosphere) | INITIATOR | CO-INHIBITOR | INDUCTION PERIOD (hour) |
|---|---|---|---|---|
| G (6/5) | 70 (air) | $Bz_2O_2$, 0.3% | Mn, 6 ppm | 11 |
| H (6/5) | 70 (air) | $Bz_2O_2$, 0.3% | none | 5 |
| I (3/5) | 70 (air) | $Bz_2O_2$, 0.3% | Mn, 5 ppm | 7 |
| J (3/5) | 70 (air) | $Bz_2O_2$, 0.3% | Mn, 10 ppm | 7 |
| K (3/5) | 70 (air) | $Bz_2O_2$, 0.3% | Mn, 15 ppm | 7 |
| L (3/5) | 70 (air) | $Bz_2O_2$, 0.3% | none | 4 |
| M (3/5) | 70 (air) | $Bz_2O_2$, 0.3% | Mn, 5 ppm | 9 |
| N (6/5) | 70 (air) | $Bz_2O_2$, 0.3% | PTZ, 100 ppm | 4 |
| O (3/5) | 70 (air) | $Bz_2O_2$, 0.3% | none | 5 |
| P (5/10) | 70 (nitrogen) | $Bz_2O_2$, 0.3% | Mn, 5 ppm | 0.1 (2 exploded) |
| Q (5/10) | 70 (nitrogen) | $Bz_2O_2$, 0.3% | none | 0.1 (2 exploded) |
| R (1/1) | 70 (nitrogen) | $Bz_2O_2$, 0.3% | Mn, 5 ppm | 8 |
| S (1/1) | 70 (nitrogen) | $Bz_2O_2$, 0.3% | none | 3 |
| T (1/5) | 70 (nitrogen) | $Bz_2O_2$, 0.3% | Mn, 10 ppm | 1 |
| U (1/5) | 70 (nitrogen) | $Bz_2O_2$, 0.3% | Mn, 15 ppm | 1 |
| V (1/5) | 70 (nitrogen) | $Bz_2O_2$, 0.3% | PTZ, 100 ppm | 0.1 |
| W (1/5) | 70 (nitrogen) | $Bz_2O_2$, 0.3% | HQ, 9 ppm | 0.1 |
| X (1/5) | 70 (nitrogen) | $Bz_2O_2$, 0.3% | HQ, 52 ppm | 0.1 |
| Y (1/5) | 70 (nitrogen) | $Bz_2O_2$, 0.3% | HQ, 102 ppm | 0.1 |

TABLE 2-continued

| CASE (# samples run/ sample size, cc) | TEMP., ° C. (Atmosphere) | INITIATOR | CO-INHIBITOR | INDUCTION PERIOD (hour) |
|---|---|---|---|---|
| Z (3/5) | 60 (air) | AIBN, 0.12% | Mn, 5 ppm | >29 ss |
| AA (3/5) | 60 (air) | AIBN, 0.12% | Mn, 10 ppm | >29 ss |
| BB (3/5) | 60 (air) | AIBN, 0.12% | Mn, 15 ppm | >29 ss |
| CC (3/5) | 60 (air) | AIBN, 0.12% | none | 18 |

HQ = hydroquinone; AIBN = azobisisobutyronitrile; $Bz_2O_2$ = benzoyl peroxide 0.3 wt % benzoyl peroxide ($Bz_2O_2$, a free-radical initiator) was added to glacial acrylic acid and stability was tested at 70° C. under air (case H, Table 2). The mixture polymerized after an average of 5 hours. In a second test (case G) containing 5 ppm manganese and 0.3 wt % benzoyl peroxide, the average induction period was 11 hours. In case L, control samples averaged a 4 hour induction period whereas glacial acrylic acid samples with 5, 10 and 15 ppm manganese each (cases I,J,K) had a 7 hour induction period. As observed earlier, concentrations of manganese higher than 5 ppm do not seem to impart any more stability than does 5 ppm. In cases M–O, the samples all contained 0.3 wt % $Bz_2O_2$; the control samples (case O, no Mn or PTZ) polymerized in about 5 hours, the PTZ samples in 4 hours and the manganese-containing samples in 9 hours.

Although these results do not demonstrate super-stabilization by Mn against $Bz_2O_2$ initiation, the addition of manganese did significantly increase the stability of glacial acrylic acid to free-radical polymerization and was clearly a better co-inhibitor than PTZ (i.e. induction periods for Mn and PTZ were 9 and 4 hours respectively).

Cases P–Q were conducted in the same manner as cases G–H above, except that oxygen had been scrupulously removed and the study conducted under a nitrogen blanket. In these experiments, the reaction vessels were almost liquid full. Case P, manganese-containing and case Q, manganese-free, both polymerized explosively after about 6 minutes of heating. This experiment was rerun using one-tenth the sample size (1 cc; cases R&S). Case S, manganese-free sample polymerized after 3 hours and case R, manganese-containing sample polymerized after 8 hours.

Cases T,U&V were conducted in the same manner as cases R&S except using 5 cc samples. Manganese was present at 10 ppm (case T) or 15 ppm (case U). In case V 100 ppm PTZ was used. In cases T&U the manganese-containing samples took 1 hour to polymerize whereas in case V the PTZ containing sample polymerized within 5 minutes. Cases W,X&Y were conducted for a direct comparison with hydroquinone (HQ) as a coinhibitor. Samples containing 9, 52 and 102 ppm HQ, case W,X,Y respectively (along with about 200 ppm MEHQ) were studied under the same conditions as cases T,U,V. In each case, the induction period was less than 4 minutes. These results illustrate the superiority of Mn as a coinhibitor as compared to HQ.

In evaluation the results of cases P–Y, heat transfer, total volume of gas evolution ($Bz_2O_2$ evolves carbon dioxide on decomposition) and free space in the sample tubes may have played a role in determining the rate and brisance of the polymerization of acrylic acid with benzoyl peroxide in the absence of oxygen. From the above results we conclude that Mn coinhibitor is effective in stabilizing glacial acrylic acid containing a polymerization initiator only if oxygen is present.

Mn coinhibitor super-stabilizes acrylic acid against thermally initiated polymerization either in the presence or absence of oxygen. However, it appears to be ineffective in cases where oxygen is absent and acrylic acid ($\alpha,\beta$-unsaturated carboxylic acid) is contaminated with a free radical initiator such as peroxide.

In cases T–Y (run under equivalent conditions) 10 ppm or 15 ppm manganese was a much better coinhibitor than either 100 ppm of either PTZ or HQ.

Cases Z–CC were carried out using 0.12 wt % azobisisobutyronitrile (AIBN) as a polymerization initiator. AIBN is a free-radical initiator which produces carbon-centered radicals in contrast to benzoyl peroxide, which produces oxygen-centered radicals. These runs were carried out at 60° C. under air. The manganese-free samples (case CC) had an average induction period of 18 hours; the manganese-containing samples (cases Z–BB) did not polymerize during the length of the experiment, i.e. greater than 29 hours of heating. Thus samples representing cases Z–BB exhibited super-stabilization.

These results indicate that manganese enhances the stability of acrylic acid that has become contaminated with an oxygen radical or a carbon radical producing compound. Explosive polymerization resulted from a combination of oxygen radical producing compound and lack of oxygen in the blanket atmosphere. In cases M,N,T,U,V,W,X, and Y the stability of acrylic acid containing manganese was equal to or greater than that containing 100 ppm of either PTZ (cases M,N,T,U, and V) or HQ (case W,X and Y).

EXAMPLE 4

Removal of Coinhibitor

The present inventor determined from inverse emulsion polymerization application tests that 100 ppb manganese is about a level at which the manganese had no negative impact on the average molecular weight or yield of an ultra high molecular weight acrylic acid polymer of the type used in the water treatment and secondary oil recovery markets. The level of 100 ppb has therefore been used as a target concentration for removal of manganese from $\alpha,\beta$-unsaturated carboxylic acid following storage and/or transport.

Studies were conducted where acrylic acid containing 5 ppm manganese was passed down an Amberlyst-15 ion exchange resin bed (Rohm & Haas, Philadelphia, Pa.) with a 15 minute contact time. It was determined that 4400–5000 bed volumes could be successfully treated before the manganese breakthrough concentration (concentration of Mn in the treated acid) reached 100 ppb. In a further study, 3100 bed volumes were treated before the 100 ppb manganese breakthrough was reached.

Another ion exchange resin, Amberlyst IRC-50 (Rohm & Haas), was found to remove manganese, however, less effectively than the Amberlyst-15. A further phosphonate-based resin, Diphonix, was found to be ineffective.

A resin bed of Amberlyst-15 was loaded with manganese cation (from the removal of manganese cation from manganese-containing acrylic acid) to study the feasibility of regenerating the resin. The bed in question was rapidly loaded with manganese by passing through it about 337 g of glacial acrylic acid containing about 2011 ppm manganese (equivalent to 4313 bed volumes of glacial acrylic acid containing 5 ppm manganese). Discounting the manganese exiting with the effluent, the bed had absorbed about 0.66 g manganese. The effluent acrylic acid was found to have the same concentration of dimer as the column feed. This indicates that the acid sites on Amberlyst-15 do not catalyze dimer formation in acrylic acid under these conditions. On treatment with about 947 g (31 bed volumes) of 4 wt % aqueous sulfuric acid, about 74% of the manganese was recovered from the resin bed. The regenerated bed was used for manganese removal to confirm the regeneration. 898 g (29 bed volumes) acrylic acid containing 5 ppm Mn was passed through the regenerated resin bed. No Mn could be detected in the treated acid.

All of the compositions and methods disclosed and claimed herein can be made and executed without undue experimentation in light of the present disclosure. While the compositions and methods of this invention have been described in terms of preferred embodiments, it will be apparent to those of skill in the art that certain agents which are chemically related may be substituted for the agents described herein without departing from the concept, spirit and scope of the invention. All such similar substitutions and modifications apparent to those skilled in the art are deemed to be within the spirit, scope and concept of the invention as defined by the appended claims.

What is claimed is:

1. A process for inhibiting free-radical polymerization of an α,β-unsaturated carboxylic acid, and providing desired grade α,β-unsaturated carboxylic acid for use following storage and transport, comprising:

combining the α,β-unsaturated carboxylic acid with a phenolic inhibitor and a coinhibitor to form an inhibited mixture;

storing the inhibited mixture;

transporting the inhibited mixture; and removing the coinhibitor to provide the desired grade α,β-unsaturated carboxylic acid for use, wherein the coinhibitor is a metal cation having at least two valence states which are interconvertible via electron transfer reactions with other species in the mixture, and wherein the α,β-unsaturated carboxylic acid has structure I:

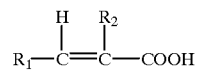

wherein
   $R_1$ is H, or $C_{1-9}$ alkyl or cycloalkyl; and
   $R_2$ is H, or methyl.

2. The process of claim 1 wherein $R_1$ and $R_2$ are H.

3. The process of claim 1 wherein $R_1$ is H, and $R_2$ is methyl.

4. The process of claim 1 wherein the metal cation is a cation selected from the group consisting of manganese, copper, chromium, iron and cerium.

5. The process of claim 4 wherein the metal cation is a cation of manganese.

6. The process of claim 5 wherein the manganese is present in the inhibited mixture at a concentration of 0.1 ppm to 100 ppm.

7. The process of claim 5 wherein the manganese is present in the inhibited mixture at a concentration of 1 ppm to 50 ppm.

8. The process of claim 5 wherein the manganese is present in the inhibited mixture at a concentration of 2 ppm to 20 ppm.

9. The process of claim 1 wherein the phenolic inhibitor is selected from the group consisting of phenol, hydroquinone, and p-methoxyphenol.

10. The process of claim 9 wherein the phenolic inhibitor is p-methoxyphenol.

11. The process of claim 10 wherein the p-methoxyphenol is present in the inhibited mixture at a concentration of between about 10 ppm to 1500 ppm.

12. The process of claim 11 wherein the p-methoxyphenol is present in the inhibited mixture at a concentration of 20 ppm to 1000 ppm.

13. The process of claim 12 wherein the p-methoxyphenol is present in the inhibited mixture at a concentration of 50 ppm to 600 ppm.

14. The process of claim 1 wherein the α,β-unsaturated carboxylic acid is glacial acrylic acid.

15. The process of claim 1 wherein the transporting is by marine shipment.

16. The process of claim 1 wherein the transporting is by land shipment.

17. The process of claim 1 wherein removing the coinhibitor is by use of a cation ion exchange resin.

18. The process of claim 17 wherein the cation exchange resin has sulfonic acid functional groups.

19. The process of claim 1 wherein the α,β-unsaturated carboxylic acid is glacial acrylic acid, the phenolic inhibitor is p-methoxyphenol, and the coinhibitor is a manganese cation.

20. The process of claim 1 wherein the combining is during production of the α,β-unsaturated carboxylic acid.

21. A process for inhibiting free-radical polymerization of an α,β-unsaturated carboxylic acid for storage and transport, the acid inadvertently contaminated with a polymerization initiator, comprising:

combining the α,β-unsaturated carboxylic acid with a phenolic inhibitor and a coinhibitor in the presence of air to form an inhibited mixture;

storing the inhibited mixture; and transporting the inhibited mixture;

wherein the coinhibitor is a metal cation having at least two valence states which are interconvertible via electron transfer reactions with other species in the mixture, and wherein the α,β-unsaturated carboxylic acid has structure I:

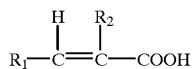

wherein $R_1$ is H, or $C_{1-9}$ alkyl or cycloalkyl; and $R_2$ is H, or methyl.

22. The process of claim 21 further comprising removing the coinhibitor to provide a desired grade of α,β-unsaturated carboxylic acid for use after storage and transport.

23. The process of claim 21 wherein $R_1$ and $R_2$ are H.

24. The process of claim 21 wherein $R_1$ is H, and $R_2$ is methyl.

25. The process of claim 21 wherein the metal cation is a cation selected from the group consisting of manganese, copper, chromium, iron and cerium.

26. The process of claim 25 wherein the metal cation is a cation of manganese.

27. The process of claim 21 wherein the phenolic inhibitor is selected from the group consisting of phenol, hydroquinone, and p-methoxyphenol.

* * * * *